United States Patent [19]

Otani et al.

[11] Patent Number: 5,697,980
[45] Date of Patent: Dec. 16, 1997

[54] ARTIFICIAL FILLING AND PROSTHETIC MATERIAL

[76] Inventors: Sugio Otani, 2010-2, Kurokawa, Hishi-machi, Kiryu-shi, Gunma-ken; Sadakatsu Yanagisawa, 3-34-407 Mita 2-chome, Minato-ku, Tokyo; Kunio Niijima, No. 563, Kamiko-machi, Omiya-shi, Saitama-ken; Kazusi Matuura, 4-18-24-107, Soshigaya, Setagaya-ku, Tokyo; Hirosi Machino, 5-1-619, Tsutsujigaoka, Midori-ku, Yokohama-shi, Kanagawa-ken; Toru Fuse, 2445, Oyama-cho, Machida-shi, Tokyo, all of Japan

[21] Appl. No.: 459,630

[22] Filed: Jun. 2, 1995

Related U.S. Application Data

[63] Continuation of Ser. No. 147,446, Nov. 5, 1993, abandoned, which is a continuation of Ser. No. 868,885, Apr. 16, 1992, abandoned.

[30] Foreign Application Priority Data

Apr. 19, 1991 [JP] Japan ............... 3-088670

[51] Int. Cl.$^6$ .................. A61F 2/28; A61F 2/54
[52] U.S. Cl. ........................ 623/16; 623/66
[58] Field of Search ............... 623/16, 18, 66; 424/422, 423, 424, 425

[56] References Cited

U.S. PATENT DOCUMENTS

| | | | |
|---|---|---|---|
| 4,070,514 | 1/1978 | Eatherly et al. | 623/16 |
| 4,192,021 | 3/1980 | Diebiq et al. | 623/16 |
| 4,457,984 | 7/1984 | Otani et al. | |
| 4,636,526 | 1/1987 | Dorman et al. | 623/16 |
| 4,645,503 | 2/1987 | Lin et al. | 623/16 |
| 4,713,076 | 12/1987 | Draenert et al. | 623/16 |
| 4,794,023 | 12/1988 | Shimamune et al. | |
| 4,795,472 | 1/1989 | Crowinshield et al. | 623/18 |
| 4,842,603 | 6/1989 | Draenert et al. | 623/16 |
| 4,842,604 | 6/1989 | Dorman et al. | 623/16 |
| 4,863,472 | 9/1989 | Törmälä et al. | 623/16 |
| 4,863,475 | 9/1989 | Andersen et al. | 623/16 |
| 4,965,088 | 10/1990 | Shimamune et al. | 623/16 |
| 4,976,736 | 12/1990 | White et al. | 623/16 |
| 5,013,323 | 5/1991 | Kobayashi et al. | 623/16 |
| 5,064,439 | 11/1991 | Chang et al. | 623/16 |
| 5,171,326 | 12/1992 | Ducheyne et al. | 623/66 |

*Primary Examiner*—Debra S. Brittingham
*Attorney, Agent, or Firm*—Oblon, Spivak, McClelland, Maier & Neustadt, P.C.

[57] ABSTRACT

An artificial filling and prosthetic material, characterized in that the surface of a substrate is coated with a calcium phosphate compound together with a water-insoluble and bio-degradable binder polymer. This material is capable of firmly adhering to tissue for a short time.

6 Claims, No Drawings

ARTIFICIAL FILLING AND PROSTHETIC MATERIAL

This application is a Continuation of application Ser. No. 08/147,446, filed on Nov. 5, 1993, now abandoned, which is a Continuation of application Ser. No. 07/868,885, filed on Apr. 16, 1992, now abandoned.

BACKGROUND OF THE INVENTION

1. Field of the Invention

The present invention relates to an artificial filling and prosthetic material, in particular, to an artificial material for filling broken-off parts of teeth or bones and subjecting the same to prosthesis.

2. Prior Art

It is conventional to fill broken-off parts of teeth or bones and/or to subject them to prosthesis by using an artificial material. The artificial materials hitherto applied to a living body include metallic materials, organic materials, inorganic materials and the like. However, they still have some problems regarding e.g., strength, safety, affinity with a living body and adhesion. Therefore, further researches have still been made to discover or develop a material which is more similar to normal teeth or bones.

When broken-off parts of teeth or bones are filled or subjected to prosthesis using an artificial material, it is in particular important that the artificial materials adhere firmly to a living body. In this art the adhesion is a conventional subject to be improved. At present this adhesion is such a degree that the artificial material stably fixes to tissue at 2 to 3 months after the artificial material is embedded. Known materials improving the adhesion are bioactive materials such as hydroxyapatite and tricalcium phosphate.

It is believed that these bioactive materials are integrated with apatite produced by osteoblast in a living body, so as to adhere to normal bones. The bioactive materials are however mainly made of ceramic materials which have insufficient strength. Consequently they are relatively low in strength, as compared with a natural bone, and their strength sharply decreases extremely when a scratch is generated on their surfaces.

On the other hand, bio-inert materials such as metallic materials, carbon materials, alumina and zirconia are superior to a natural bone in strength. However, they are inferior to the bioactive materials in adhesion to the osseous tissue.

Accordingly, in order to improve such adhesion, for example, the following approaches have been suggested: A method in which unevenness is provided on the surfaces of an artificial materials; and a method in which a porous structure layer is provided on the surfaces of an artificial material to form connective tissue similar to that of a living body, thereby causing strong adhesion by a reaction of the porous layer with the living body (JP-B-No. 9859/86).

Although the known bioactive materials or bio-inert materials respectively exhibit a specific adhesion property to a living body, both require a long time as much as 2 to 3 months for substantially complete adhesion. In addition, these artificial materials have to be kept free from movement during the above period. If they are kept insufficiently free from moving, the time required for adhesion becomes longer and the adhesion becomes impossible due to the occurrence of inflammation.

An object of the present invention is to provide a high quality of an artificial filling and prosthetic material capable of adhering for a shorter time.

Another object of the invention is to provide an artificial filling and prosthetic material capable of strong adhesion.

To accomplish these objects, the present inventors have found that when the surfaces of a substrate are coated with a calcium phosphate compound together with a water-insoluble and bio-degradable binder polymer, the adhesion of the resultant materials is improved and the time required for adhesion is shortened to a large extent.

SUMMARY OF THE INVENTION

This invention is therefore an artificial filling and prosthetic material characterized in that the surface of its substrate is coated with a calcium phosphate compound together with a water-insoluble and bio-degradable binder polymer.

Best Embodiments of the Invention

The present invention will be described in more detail in the following.

The substrate to be used in the present invention can be selected from any base materials which are conventionally used in this field. Thus, there is no restriction about the base materials. The substrate typically includes carbonaceous materials such as various carbon fiber reinforced carbon materials, sintered carbon materials and glassy carbon materials; metals such as platinum, titanium, tantalum and tungsten; and ceramic materials such as alumina, zirconia, calcium phosphate, titania and biological glass. It is preferred to use the carbon fiber reinforced carbon materials, titanium or alumina since they improve both the strength of the artificial prosthetic material and the affinity thereof for a living body.

If the substrate to be embedded in a living body has a porous surface, tissue penetrates into any pores in the substrate to form strong connective tissue, which is preferred. Furthermore, in this case, the pores keep therein the water-insoluble and bio-degradable binder polymer and the calcium phosphate compound, even when they are removed from the surface of the substrate. Thus, the kept two components provide their desired effects. This permits the material according to the invention to be handled more easily.

In particular, it is more preferred to use such porous materials that connective tissue can calcify and can change into osseous tissue. Specific examples of these porous materials include a porous layer of alumina; and a porous carbon layer formed by depositing thermally-decomposed carbon on a non-woven cloth of carbon fibers. The porous layer of alumina is described in e.g., JU-B-No. 34731/81. This is prepared as follows: organic binders (e.g., spherical bodies of polyvinyl alcohol, polyethylene or the like; or chopped fibers) are added to $Al_2O_3$ powder to form a molded body, followed by burning off said organic binder from the body under the sintering or quasi-sintering temperature of the body and further burning or sintering the body, thereby obtaining a porous layer having open pores.

A method for obtaining the porous carbon layer to be used is specifically described in detail in e.g., JP-B-No. 9859/86. This method is as follows: a woven cloth, non-woven cloth, felt or paper, each formed from relatively long carbon fibers, or chopped strand using relatively short carbon fibers are coated and fixed onto the surface of a core material. The core is a member which has a strength such that these fibers can cover and can be fixed thereto. The fibers are, for example, a carbonaceous material or a metal such as Ti or Pt. Upon coating, in the case of using the woven cloth, non-woven cloth, felt or paper, the material is cut into a suitable size, and is adhered to the core using an organic adhesive if necessary. Furthermore, an optional approach is to firmly fix the cloth, paper and the like on the core by winding long fibers thereon. In the case of using the chopped strands, an organic adhesive is applied beforehand to desired parts of the core surface, after which the chopped strands adheres to the parts and are fixed thereon in such a manner that the strands are sprinkled on the surface. Then, on the obtained body, thermally-decomposed carbon is precipitated or deposited so that it integrates with this body. In order to form an excellent porous carbon layer, it is preferred to carry out a treatment in which thermally-decomposed carbon is precipitated in such a manner that the thermally-decomposed carbon is deposited at a temperature from 600° C. to 2300° C., preferably from 700° to 1100° C. and in a state having a negative temperature-gradient in the direction from the interior of a core to its surface.

The carbon porous layer typically has a structure in which the multiple fibers overlap e.g., in random directions and strongly adhere to each other. The diameters of the formed pores are not less than 100 μm preferably not less than 200 μm in the vicinity of the substrate surface. It is preferred that the pore diameters become smaller toward the interior the substrate, that is, that a porous layer has the void distribution such that the void ratio gradually decreases toward the interior.

In the case of preparing the artificial material for dental implant, it is preferred to provide a part of the substrate with a screw structure or with a non-circular cross sectional part having a non-screw structure since dropping-out of the artificial material is avoided physically.

As already described, the present invention is characterized in that the surface of a substrate is coated with a calcium phosphate compound together with a water-insoluble and bio-degradable binder polymer.

The calcium phosphate compound is any compound which contains Ca and P. A part of its chemical structure may be substituted by another atom or an atomic group. Examples of the calcium phosphate compounds include dicalcium phosphate anhydride($CaHPO_4$), calcium pyrophosphate ($Ca_2P_2O_7$), brushite ($CaHPO_4 2H_2O$), tricalcium phosphate ($Ca_3(PO_4)_2$), and hydroxyapatite (HAp: $Ca_{10}(PO_4)_6(OH)_2$); fluoroapatite (FAp: $Ca_{10}(PO_4)_6F_2$, francolite (carbonate containing FAp), and dahllite (carbonate containing HAp). In particular, tricalcium phosphate, hydroxyapatite and mixtures thereof are preferred because of their strong bone inducing action, but there is not limitation to these compounds.

The bone inducing action which is exhibited by the calcium phosphate compound means the action to facilitate growth of fibrous tissue on the surface of the substrate and to facilitate the change thereof to osseous tissue. Especially, when the surface of the substrate is porous, the action well contributes to achieving strong adhesion, since the action promotes to formation of a double network structure in which tissue and fibers of the porous materials intertwine.

The calcium phosphate compound is used in an amount which is sufficient to exhibit the above bone inducing action. More particularly, it is appropriate to use in an amount capable of forming a layer of not less than 0.1 μm in thickness on the surface of the substrate.

When the surface of the substrate is porous, it is appropriate to use the calcium phosphate compound at least in an amount that a layer of not less than 0.1 μm in thickness can form on the pore surface in the vicinity of the surface of the substrate. More preferably, the calcium phosphate compound should be formed at a thickness of not less than 0.1 μm on both the surface of the substrate and the pore surface is in the interior of the substrate. However, if the amount of the calcium phosphate compound to be coated is an amount which blocks the pores, the penetration of tissue into the pores might be badly impeded.

The water-insoluble and bio-degradable binder polymer is one which is water-insoluble, has binding ability and has bio-degradability.

As the water-insoluble and bio-degradable binder polymer, any known biodegradable polymers can be used. Examples of the biodegradable polymer include poly(3-hydroxybutylate-4-hydroxybutylate), poly-3-hydroxybutylate, poly(3-hydroxy-butyrate-3-hydroxyvalerate), polylactic acid, polycaprolactone, polyethyleneadipate, polybutyleneadipate, and polyhydroxyalkanoate.

In particular, polyhydroxybutylate (PHB), polylactic acid, polycaprolactone and polyhydroxalkanoate are especially preferred since they are readily soluble in an organic solvent such as chloroform and are not soluble in water. They can easily adhere to the surface of the substrate by being applyed thereto after being dissolved in the organic solvent. If the binder polymer is water-soluble, it dissolves in a humor. Consequently, the calcium phosphate compound is removed from the substrate surface and such desired effects as bone inducing action are not accomplished. In contrast to this, there is not such a fear concerning PHB, polylactic acid and the like.

Preferably, the water-insoluble and bio-degradable binder polymer is used in an amount such that it is sufficient to bind the calcium phosphate compound particles to each other and bind the calcium phosphate compound particles to the substrate, and such that it is appropriate not to spoil, due to the complete covering of the surface of the calcium phosphate compound, the bone inducing action. More specifically, the water-insoluble and bio-degradable binder polymer is used in an amount of 2–50% by weight, preferably 5–30% by weight, of the calcium phosphate compound.

Using the water-insoluble and bio-degradable binder polymer of the invention permits adherence in much shorter time, as compared with the case in which only the calcium phosphate compound is used. This may be because the water-insoluble and bio-degradable binder polymer promptly change into tissue because of decomposition and absorption of the binder polymer into a living body.

There is no limitation about the method for coating the substrate surface with the calcium phosphate compound together with the water-insoluble and bio-degradable binder polymer. However, the following manner is free from being influenced by the surface state of the substrate, so that it is easy and efficient: the manner in which a slurry in which the calcium phosphate compound is dispersed in a specific solution(i.e., the solution comprising the water-insoluble and bio-degradable binder polymer dissolved in an appropriate solvent) is applied to the surface of the substrate by means of dip coating, spray coating or the like.

When the substrate surface is porous, it is preferred to use the method in which the above slurry is dip coated. This is because only the solvent is evaporated after the impregnation of the slurry into the pores, so that even the interior of the pores can be coated without the loss of the porosity of the substrate. Furthermore, it is more preferred to make use of the vacuum impregnation method of placing the substrate in a container, removing the air or the like from their pores by decreasing the pressure therein, and thereafter subjecting the substrate to impregnation at an ambient pressure or at a high pressure.

In this invention, components for coating the surface of the substrate are not limited to the calcium phosphate compound and the water-insoluble and bio-degradable binder polymer. Other components may be added, if necessary.

For example, in the preparation of a coating slurry, it is appropriate to use dispersants such as glucose aliphatic acid ester, glycerin monostearate (MSG), sorbitan sesquioleate and the like if necessary, in order to avoid uneven coating of the calcium phosphate compounds or to avoid stoppage of the surface pores by aggregated lumps.

In the same preparation, the order of mixing the binder and the dispersants is important since it affects the dispersibility of the calcium phosphate compound. A part of a dispersing medium in which the calcium phosphate compound and the dispersant are dissolved is subjected to a dispersing and crushing treatment for a predetermined time in a dispersing container. Thereafter, to the resultant material is added another dispersing medium in which the binder is dissolved, which is again subjected to a dispersing and crushing treatment. A conventional ball mill, vibrating ball mill, paint shaker or the like is used for the dispersing and crashing treatment.

If the substrate is made of, for example, the porous layer, a slurry dispersed as described above is impregnated into the porous layer. More particularly, in order to impregnate a slurry into the interior of the porous layer, it is convenient to introduce the slurry toward the substrate after decreasing the pressure around it and then increase the pressure to ambient pressure after a predetermined time.

EXAMPLES

In the following, the present invention will be explained in more detail with reference to examples. However, the present invention is not restricted to these examples unless the scope and spirit of the invention is exceeded.

Example 1

A core material of titanium was provided which was composed of a bar-like head part of 3.2 mm in diameter and 1.5 mm in length with a bar-like leg part of 1.9 mm in diameter and 9.5 mm in length thereunder. A felt of carbon fibers was wound to a thickness of 5 mm round the leg part. This sample was heated in a reaction vessel to the temperature of 700° C. by means of high frequency induction heating, thereafter vapor of dichloroethylene was introduced inside reaction vessel using argon gas as a carrier gas in order to generate thermally-decomposed carbon. After the reaction for one hour, a material was obtained in which the titanium core material was combined and integrated with the carbon fibers by the thermally-decomposed carbon. This material also had a porous structural layer having open pores on its surface. By adjusting the surface state of this material using a grinder for fine processing, a substrate was obtained in which a titanium head part of 3.2 mm in diameter and 11.6 mm in length had hereunder a porous carbon structural layer having open pores on its surface.

Two grams of hydroxy apatite (HAP) having an average diameter of 2 μm, 0.1 g of glycerine monostearate (MSG), 40 g of chloroform, 0.4 g of polyhydroxybutylate (PHB) and 57.5 g of chloroform together with 70 g of dispersing balls were charged in a container, the volume of which was 140 ml, and were subjected to a paint shaker treatment for 6 hours. After dispersing HAP in the chloroform, a slurry composed of HAP 2/MSG 0.1/PHB 0.4/chloroform 97.5 (each weight %) was obtained.

The slurry was vacuum-impregnated into the above substrate having the carbon porous layer, which was then dried to produce an artificial filling and prosthetic material coated with HAP. When the surface and interior of the pores of this filling and prosthetic material were observed using a scanning electron microscope (SEM), The formation of a HAP layer having a thickness of ca.2 μm in the vicinity of the surface and 0.1 μm in the interior was observed. No pores were blocked.

In addition, said filling and prosthetic material was embedded in a femur of a Japanese ape. The ape was sacrificed after a certain time, and said femur was taken removed to measure the shear attachment strength between the femur and said filling and prosthetic material, using a mechanical property analysis apparatus "TCM5000A" manufactured by Minebea Co. The results are shown in Table 1.

Comparative Example 1

An experiment was carried out similar to Example 1 except that a substrate produced in the same manner as in Example 1 was embedded without being coated with HAP in a thighbone of a Japanese ape. The results are shown in Table 1.

Comparative Example 2

A material was prepared and shear attached strength was measured in a similar manner to Example 1 except that a non-biodegradable polymer carboxymethyl cellulose was used instead of polyhydroxybutylate and a slurry having a composition of HAP 10/sodium carboxymethyl cellulose 0.2/water 89.9 (each weight %) was used as a slurry to be impregnated to the substrate. The results are shown in Table 1.

TABLE 1

| | Shear Strength (Japanese Ape Femur) | | |
|---|---|---|---|
| Embedding Time/Week | HAP-Coating By Water-Insoluble and Bio-degradable Polymer (Example 1) | No Coating (Comparative Example 1) | HAP-Coating By Water-Soluble Polymer (Comparative Example 2) |
| 10 | 226 | 79 | 85 |
| 13 | 347 | 230 | — |
| 19 | 379 | 294 | 262 |

The artificial filing and prosthetic material of the present invention is capable of adhering to living bodies more strongly and for a shorter time than conventional ones, and can be produced easily, so that it provides many industrial advantages.

What is claimed is:

1. A strongly adhering artificial filling and prosthetic material, comprising:
    a substrate having a porous surface selected from the group consisting of porous carbon fiber, reinforced carbon material, porous titanium and porous aluminum; and
    a coating on and into said porous surface of said substrate, which coating comprises an admixture of a calcium phosphate compound and a water-insoluble and bio-degradable binder polymer in an amount of 5–30% by weight on the basis of the calcium phosphate compound, and is prepared by means of dip-coating, spray-coating or vacuum-impregnation of the porous surface using a slurry comprising said calcium phosphate compound, said water-insoluble and bio-degradable polymer and an organic solvent.

2. The artificial filling and prosthetic material of claim 1, wherein said water-insoluble and bio-degradable binder polymer contains at least one polymer selected from the group consisting of poly(3-hydroxybutyrate-4-hydroxybutyrate), poly-3-hydroxybutyrate, poly(3-hydroxybutyrate-3-hydroxyvalerate), polylactic acid, polyglycolic acid, polycaprolactone, polyethyleneadipate, polybutyleneadipate and polyhydroxyalkanoate.

3. The artificial filling and binding material of claim 1, wherein said water-insoluble and bio-degradable binder polymer contains at least one polymer selected from the group consisting of polyhydroxybutyrate and polylactic acid.

4. The artificial filling and binding material according to claim 1, wherein said calcium phosphate compound contains at least one compound selected from the group consisting of calcium secondary phosphate anhydride ($CaHPO_4$), calcium pyrophosphate ($Ca_2P_2O_7$), brushite ($CaHPO_4 \cdot 2H_2O$), tricalcium phosphate ($Ca_3(PO_4)_2$) and hydroxyapatite ($Ca_{10}(PO_4)_6(OH)_2$).

5. The filling and prosthetic material according to claim 1, wherein said calcium phosphate compound contains at least one compound selected from the group consisting of tricalcium phosphate and hydroxyapatite.

6. The artificial filling and prosthetic material according to claim 1, wherein said substrate surface is porous carbon fiber reinforced carbon material.

* * * * *

UNITED STATES PATENT AND TRADEMARK OFFICE
CERTIFICATE OF CORRECTION

PATENT NO.    : 5,697,980
DATED         : December 16, 1997
INVENTOR(S)   : Sugio Otani, et. al.

It is certified that error appears in the above-identified patent and that said Letters Patent is hereby corrected as shown below:

Title page, item {73], Assignee: should read as following:
--Mitsubishi Chemical Corporation, Tokyo; Research Development Corporation of Japan, Tokyo; all of Japan--. (Part Interest)

Signed and Sealed this

Twenty-fourth Day of February, 1998

Attest:

BRUCE LEHMAN

*Attesting Officer*          *Commissioner of Patents and Trademarks*